United States Patent
Vollmer

(10) Patent No.: US 7,968,511 B2
(45) Date of Patent: Jun. 28, 2011

(54) COMBINATION THERAPY WITH GLATIRAMER ACETATE AND MITOXANTRONE FOR THE TREATMENT OF MULTIPLE SCLEROSIS

(75) Inventor: Timothy Vollmer, Scottsdale, AZ (US)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 637 days.

(21) Appl. No.: 10/556,454

(22) PCT Filed: May 14, 2004

(86) PCT No.: PCT/US2004/015225
§ 371 (c)(1),
(2), (4) Date: Dec. 13, 2006

(87) PCT Pub. No.: WO2004/103297
PCT Pub. Date: Dec. 2, 2004

(65) Prior Publication Data
US 2007/0173442 A1    Jul. 26, 2007

Related U.S. Application Data

(60) Provisional application No. 60/470,640, filed on May 14, 2003.

(51) Int. Cl.
*A61K 38/00* (2006.01)
*A61K 51/00* (2006.01)
*A61K 31/33* (2006.01)
(52) U.S. Cl. ......... 514/1.1; 514/183; 514/309; 514/310; 514/319; 514/331; 424/1.69
(58) Field of Classification Search ........................ None
See application file for complete search history.

(56) References Cited

U.S. PATENT DOCUMENTS

| | | | | |
|---|---|---|---|---|
| 4,617,319 A | * | 10/1986 | Kerwar et al. | 514/647 |
| 6,214,791 B1 | * | 4/2001 | Arnon et al. | 514/2 |
| 6,531,464 B1 | * | 3/2003 | Szabo et al. | 514/183 |

OTHER PUBLICATIONS

International Search Report issued by the International Searching Authority on Jan. 31, 2005 in connection with International Application No. PCT/US2004/015225.
Written Opinion Of The International Searching Authority issued by the International Searching Authority on Jan. 31, 2005 in connection with International Application No. PCT/US2004/015225.

* cited by examiner

*Primary Examiner* — Maury Audet
(74) *Attorney, Agent, or Firm* — John P. White; Cooper & Dunham LLP

(57) ABSTRACT

The subject invention provides a method of treating a subject afflicted with a form of multiple sclerosis comprising periodically administering to the subject an amount of glatiramer acetate and an amount of mitoxantrone, wherein the amounts when taken together are effective to alleviate a symptom of the form of multiple sclerosis in the subject so as to thereby treat the subject. The subject invention also provides a package comprising glatiramer acetate, mitoxantrone and instructions for use of the together to alleviate a symptom of a form of multiple sclerosis in a subject. Additionally, the subject invention provides a pharmaceutical composition comprising an amount of glatiramer acetate and an amount of mitoxantrone, wherein the amounts when taken together are effective to alleviate a symptom of a form of multiple sclerosis in a subject. The subject invention further provides a pharmaceutical combination comprising separate dosage forms of an amount of glatiramer acetate and an amount of mitoxantrone, which combination is useful to alleviate a symptom of a form of multiple sclerosis in a subject.

7 Claims, No Drawings

COMBINATION THERAPY WITH GLATIRAMER ACETATE AND MITOXANTRONE FOR THE TREATMENT OF MULTIPLE SCLEROSIS

This application is a §371 National Stage of PCT International Application No. PCT/US2004/015225, filed May 14, 2004, claiming priority of U.S. Provisional Application No. 60/470,640, filed May 14, 2003, the contents of all of which are hereby incorporated by reference.

FIELD OF THE INVENTION

The subject invention relates to combination therapy for treating multiple sclerosis.

BACKGROUND OF THE INVENTION

One of the more common neurologic diseases in human adults is multiple sclerosis. This condition is a chronic, inflammatory CNS disease characterized pathologically by demyelination. There are five main forms of multiple sclerosis: 1) benign multiple sclerosis; 2) relapsing-remitting multiple sclerosis (RR-MS); 3) secondary progressive multiple sclerosis (SP-MS); 4) primary progressive multiple sclerosis (PP-MS); and 5) progressive-relapsing multiple sclerosis (PR-MS). Benign multiple sclerosis is characterized by 1-2 exacerbations with complete recovery, no lasting disability and no disease progression for 10-15 years after the initial onset. Benign multiple sclerosis may, however, progress into other forms of multiple sclerosis. Patients suffering from RR-MS experience sporadic exacerbations or relapses, as well as periods of remission. Lesions and evidence of axonal loss may or may not be visible on MRI for patients with RR-MS. SP-MS may evolve from RR-MS. Patients afflicted with SP-MS have relapses, a diminishing degree of recovery during remissions, less frequent remissions and more pronounced neurological deficits than RR-MS patients. Enlarged ventricles, which are markers for atrophy of the corpus callosum, midline center and spinal cord, are visible on MRI of patients with SP-MS. PP-MS is characterized by a steady progression of increasing neurological deficits without distinct attacks or remissions. Cerebral lesions, diffuse spinal cord damage and evidence of axonal loss are evident on the MRI of patients with PP-MS. PR-MS has periods of acute exacerbations while proceeding along a course of increasing neurological deficits without remissions. Lesions are evident on MRI of patients suffering from PR-MS (Multiple sclerosis: its diagnosis, symptoms, types and stages).

Researchers have hypothesized that multiple sclerosis is an autoimmune disease (Compston; Hafler and Weiner; Olsson). An autoimmune hypothesis is supported by the experimental allergic encephalomyelitis (EAE) model of multiple sclerosis, where the injection of certain myelin components into genetically susceptible animals leads to T cell-mediated CNS demyelination (Parkman). Another theory regarding the pathogenesis of multiple sclerosis is that a virus, bacteria or other agent, precipitates an inflammatory response in the CNS; which leads to either direct or indirect ("bystander") myelin destruction, potentially with an induced autoimmune component (Lampert; Martyn). Another experimental model of multiple sclerosis, Theiler's murine encephalomyelitis virus (TMEV) (Dal Canto and Lipton; Rodriguez et al.), supports the theory that a foreign agent initiates multiple sclerosis. In the TMEV model, injection of the virus results in spinal cord demyelination.

Glatiramer acetate (GA), also known as Copolymer-1, has been shown to be effective in treating multiple sclerosis (MS) (Lampert, P. W.). Daily subcutaneous injections of glatiramer acetate (20 mg/injection) reduce relapse rates, progression of disability, appearance of new lesions by magnetic resonance imaging (MRI), (Johnson, K. P. et al.) and appearance of "black holes" (Filippi, M. et al.).

COPAXONE® is the brand name for a formulation containing glatiramer acetate as the active ingredient. Glatiramer acetate is approved for reducing the frequency of relapses in relapsing-remitting multiple sclerosis. Glatiramer acetate consists of the acetate salts of synthetic polypeptides containing four naturally occurring amino acids: L-glutamic acid, L-alanine, L-tyrosine, and L-lysine with an average molar fraction in COPAXONE® of 0.141, 0.427, 0.095 and 0.338, respectively. In COPAXONE®, the average molecular weight of the glatiramer acetate is 4,700-11,000 daltons. Chemically, glatiramer acetate is designated L-glutamic acid polymer with L-alanine, L-lysine and L-tyrosine, acetate (salt). Its structural formula is:

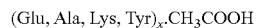

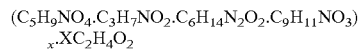

CAS-147245-92-9.

The recommended dosing schedule of COPAXONE® for relapsing-remitting multiple sclerosis is 20 mg per day injected subcutaneously (Physician's Desk Reference; see also U.S. Pat. Nos. 3,849,550; 5,800,808; 5,858,964, 5,981,589; 6,048,898; 6,054,430; 6,214,791; 6,342,476; and 6,362,161, all of which are hereby incorporated by reference).

NOVANTRONE®, the commercial embodiment of mitoxantrone, is indicated for reducing neurologic disability and/or the frequency of clinical relapses in patients with secondary (chronic) progressive, progressive relapsing, or worsening relapsing-remitting multiple sclerosis (i.e., patients whose neurologic status is significantly abnormal between relapses) NOVANTRONE® is not indicated in the treatment of patients with primary progressive multiple sclerosis (Physician's Desk Reference).

NOVANTRONE® (mitoxantrone dihydrochloride) is a synthetic antineoplastic anthracenedione for intravenous use. The molecular formula is $C_{22}H_{28}N_4O_6 \cdot 2HCl$ and the molecular weight is 517.41. The chemical name is 1,4-dihydroxy-5,8-bis[[2-[(2-hydroxyethyl)amino]ethyl]amino]-9,10-anthracenedione dihydrochloride and the structural formula is:

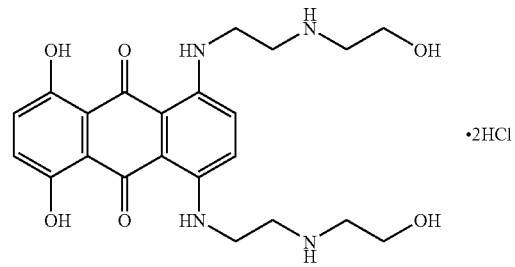

The recommended dosage of NOVANTRONE® is 12 mg/m$^2$ given as a short (approximately 5 to 15 minute) intravenous infusion every three months (Physician's Desk Reference).

The administration of two drugs to treat a given condition, such as a form of multiple sclerosis, raises a number of potential problems. In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug (Guidance for Industry. In vivo drug metabolism/drug interaction studies—study design, data analysis, and recommendations for dosing and labeling). Thus, when two drugs are administered to treat the same condition, it is unpredictable whether each will complement, have no effect on, or interfere with, the therapeutic activity of the other in a human subject.

Not only may the interaction between two drugs affect the intended therapeutic activity of each drug, but the interaction may increase the levels of toxic metabolites (Guidance for Industry. In vivo drug metabolism/drug interaction studies—study design, data analysis, and recommendations for dosing and labeling). The interaction may also heighten or lessen the side effects of each drug. Hence, upon administration of two drugs to treat a disease, it is unpredictable what change will occur in the negative side profile of each drug.

Additionally, it is accurately difficult to predict when the effects of the interaction between the two drugs will become manifest. For example, metabolic interactions between drugs may become apparent upon the initial administration of the second drug, after the two have reached a steady-state concentration or upon discontinuation of one of the drugs (Guidance for Industry. In vivo drug metabolism/drug interaction studies—study design, data analysis, and recommendations for dosing and labeling).

Thus, the success of one drug or each drug alone in an in vitro model, an animal model, or in humans, may not correlate into efficacy when both drugs are administered to humans.

In accordance with the subject invention, glatiramer acetate and mitoxantrone are effective in combination to treat a form of multiple sclerosis, specifically, relapsing-remitting multiple sclerosis.

SUMMARY OF THE INVENTION

The subject invention provides a method of treating a subject afflicted with a form of multiple sclerosis comprising periodically administering to the subject an amount of glatiramer acetate and an amount of mitoxantrone, wherein the amounts when taken together are effective to alleviate a symptom of the form of multiple sclerosis in the subject so as to thereby treat the subject.

The subject invention further provides a pharmaceutical composition comprising an amount of glatiramer acetate and an amount of mitoxantrone, wherein the amounts when taken together are effective to alleviate a symptom of a form of multiple sclerosis in a subject.

In addition, the subject invention provides a package comprising
i) a first pharmaceutical composition comprising an amount of glatiramer acetate and a pharmaceutically acceptable carrier;
ii) a second pharmaceutical composition comprising an amount of mitoxantrone and a pharmaceutically acceptable carrier; and
iii) instructions for use of the first and second pharmaceutical compositions together to alleviate a symptom of a form of multiple sclerosis in a subject.

DETAILED DESCRIPTION OF THE INVENTION

The subject invention provides a method of treating a subject afflicted with a form of multiple sclerosis comprising periodically administering to the subject an amount of glatiramer acetate and an amount of mitoxantrone, wherein the amounts when taken together are effective to alleviate a symptom of the form of multiple sclerosis in the subject so as to thereby treat the subject.

In one embodiment, the form of multiple sclerosis is relapsing-remitting multiple sclerosis.

In another embodiment, the subject is a human being.

In a further embodiment, each of the amount of glatiramer acetate when taken alone, and the amount of mitoxantrone when taken alone is effective to alleviate the symptom of the form of multiple sclerosis.

In an embodiment, either the amount of glatiramer acetate when taken alone, the amount of mitoxantrone when taken alone or each such amount when taken alone is not effective to alleviate the symptom of the form of multiple sclerosis.

In yet another embodiment, the symptom is the frequency of relapses, the frequency of clinical exacerbation, or the accumulation of physical disability.

In one embodiment, the amount of glatiramer acetate may be 10 to 80 mg; or 12 to 70 mg; or 14 to 60 mg; or 16 to 50 mg; or 18 to 40 mg; or 20 to 30 mg; or 20 mg. For each amount of glatiramer acetate, the amount of mitoxantrone may be 1-30 mg/m$^2$; or 3-25 mg/m$^2$; or 5-20 mg/m$^2$; or 7-17 mg/m$^2$; or 9-15 mg/m$^2$; or 10-14 mg/m$^2$; or 12 mg/m$^2$.

Alternatively, the amount of glatiramer acetate may be in the range from 10 to 600 mg/wqek; or 100 to 550 mg/week; or 150 to 500 mg/week; or 200 to 450 mg/week; or 250 to 400 mg/week; or 300 to 350 mg/week; or 300 mg/week.

In another embodiment, the amount of glatiramer acetate may be in the range from 50 to 150 mg/day; or 60 to 140 mg/day; or 70 to 130 mg/day; or 80 to 120 mg/day; or 90 to 110 mg/day; or 100 mg/day.

Alternatively, the amount of glatiramer acetate may be in the range from 10 to 80 mg/day; or 12 to 70 mg/day; or 14 to 60 mg/day; or 16 to 50 mg/day; or 18 to 40 mg/day; or 19 to 30 mg/day; or 20 mg/day.

In one embodiment, the periodic administration of glatiramer acetate is effected daily.

In another embodiment, the periodic administration of glatiramer acetate is effected twice daily at one half the amount.

In an additional embodiment, the periodic administration of glatiramer acetate is effected once every 3 to 11 days; or once every 5 to 9 days; or once every 7 days; or once every 24 hours.

For each administration schedule of glatiramer acetate, the mitoxantrone may be administered once every year to once every 5 years; or once every 2 years to once every 4 years; or once every 3 years. Alternatively, the mitoxantrone may be administered once every month to once every 6 months; or once every 2 months to once every 4 months; or once every 3 months. In yet another alternative, the mitoxantrone may be administered once every 10 to 50 days; or once every 15 to 40 days; or once every 20 to 30 days; or once every 25 days.

In a further embodiment, the administration of the glatiramer acetate substantially precedes the administration of the mitoxantrone.

In an added embodiment, the administration of the mitoxantrone substantially precedes the administration of the glatiramer acetate.

In one embodiment, the glatiramer acetate and the mitoxantrone may be administered for a period of time of at least 4 days. In a further embodiment, the period of time may be 5 days to 5 years; or 10 days to 3 years; or 2 weeks to 1 year; or 1 month to 6 months; or 3 months to 4 months. In yet another embodiment, the glatiramer acetate and the mitoxantrone may be administered for the lifetime of the subject.

The administration of mitoxantrone or glatiramer acetate may each independently be oral, nasal, pulmonary, parenteral, intravenous, intra-articular, transdermal, intradermal, subcutaneous, topical, intramuscular, rectal, intrathecal, intraocular, buccal or by gavage. For mitoxantrone, the preferred route of administration is intravenous. The preferred route of administration for glatiramer acetate is subcutaneous or oral. One of skill in the art would recognize that doses at the higher end of the range may be required for oral administration.

In one embodiment, the administration of the glatiramer acetate may be subcutaneous, intraperitoneal, intravenous, intramuscular, intraocular or oral and the administration of the mitoxantrone may be intravenous. In another embodiment, the administration of the glatiramer acetate may be subcutaneous and the administration of the mitoxantrone may be intravenous.

The subject invention further provides a pharmaceutical composition comprising an amount of glatiramer acetate and an amount of mitoxantrone, wherein the amounts when taken together are effective to alleviate a symptom of a form of multiple sclerosis in a subject.

In one embodiment of the pharmaceutical composition, each of the amount of glatiramer acetate when taken alone and the amount of mitoxantrone when taken alone is effective to alleviate the symptom of multiple sclerosis.

In another embodiment of the pharmaceutical composition, either of the amount of glatiramer acetate when taken alone, or the amount of mitoxantrone when taken alone or each such amount when taken alone is not effective to alleviate the symptom of multiple sclerosis.

In one embodiment of the pharmaceutical composition, the amount of glatiramer acetate may be in the range from 10 to 600 mg; or 100 to 550 mg; or 150 to 500 mg; or 200 to 450 mg; or 250 to 400 mg; or 300 to 350 mg; or 300 mg.

In a further embodiment of the pharmaceutical composition, the amount of glatiramer acetate may be in the range from 10 to 80 mg; or 12 to 70 mg; or 14 to 60 mg; or 16 to 50 mg; or 18 to 40 mg; or 19 to 30 mg; or 20 mg.

Alternatively, the amount of glatiramer acetate in the pharmaceutical composition may be in the range from 50 to 150 mg; or 60 to 140 mg; or 70 to 130 mg; or 80 to 120 mg; or 90 to 110 mg; or 100 mg.

For each amount of glatiramer acetate in the pharmaceutical composition, the amount of mitoxantrone in the pharmaceutical composition may be 1-30 mg/m$^2$; or 3-25 mg/m$^2$; or 5-20 mg/m$^2$; or 7-17 mg/m$^2$; or 9-15 mg/m$^2$; or 10-14 mg/m$^2$; or 12 mg/m$^2$.

The subject invention also provides a package comprising
i) a first pharmaceutical composition comprising an amount of glatiramer acetate and a pharmaceutically acceptable carrier;
ii) a second pharmaceutical composition comprising an amount of mitoxantrone and a pharmaceutically acceptable carrier; and
iii) instructions for use of the first and second pharmaceutical compositions together to alleviate a symptom of a form of multiple sclerosis in a subject.

In an embodiment of the package, the amount of glatiramer acetate may be in the range from 10 to 600 mg; or 100 to 550 mg; or 150 to 500 mg; or 200 to 450 mg; or 250 to 400 mg; or 300 to 350 mg; or 300 mg.

In another embodiment of the package, the amount of glatiramer acetate may be in the range from 10 to 80 mg; or 12 to 70 mg; or 14 to 60 mg; or 16 to 50 mg; or 18 to 40 mg; or 19 to 30 mg; or 20 mg.

Alternatively, the amount of glatiramer acetate in the package may be in the range from 50 to 150 mg; or 60 to 140 mg; or 70 to 130 mg; or 80 to 120 mg; or 90 to 110 mg; or 100 mg.

For each amount of glatiramer acetate in the package, the amount of mitoxantrone in the package may be 1-30 mg/m$^2$ or 3-25 mg/m$^2$; or 5-20 mg/m$^2$; or 7-17 mg/m$^2$; or 9-15 mg/m$^2$; or 10-14 mg/m$^2$; or 12 mg/m$^2$.

The subject invention further provides a pharmaceutical combination comprising separate dosage forms of an amount of glatiramer acetate and an amount of mitoxantrone, which combination is useful to alleviate a symptom of a form of multiple sclerosis in a subject.

In an embodiment of the pharmaceutical combination, each of the amount of glatiramer acetate when taken alone and the amount of mitoxantrone when taken alone is effective to alleviate the symptom of multiple sclerosis.

In an additional embodiment of the pharmaceutical combination, either of the amount of glatiramer acetate when taken alone, the amount of mitoxantrone when taken alone or each such amount when taken alone is not effective to alleviate the symptom of multiple sclerosis.

In a further embodiment, the pharmaceutical combination may be for simultaneous, separate or sequential use to treat the form of multiple sclerosis in the subject.

Formulations of the invention suitable for oral administration may be in the form of capsules, pills, tablets, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active compound or compounds.

In solid dosage forms of the invention for oral administration (capsules, tablets, pills, dragees, powders, granules and the like), the active ingredient(s) is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, calcium phosphate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of the active ingredients include pharmaceutically acceptable emulsions, microemulsioris, solutions, suspensions, syrups and elixirs. In addition to the active ingredient(s), the liquid dosage forms may contain inert dilutents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar and tragacanth, and mixtures thereof.

The pharmaceutical compositions, particularly those comprising glatiramer acetate, may also include human adjuvants or carriers known to those skilled in the art. Such adjuvants include complete Freund's adjuvant and incomplete Freund's adjuvant. The compositions may also comprise wetting agents, emulsifying and suspending agents, sweetening, flavoring, coloring, perfuming and preservative agents.

Glatiramer acetate may be formulated into pharmaceutical compositions with pharmaceutically acceptable carriers, such as water or saline and may be formulated into eye drops. Glatiramer acetate may also be formulated into delivery systems, such as matrix systems.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Example 1

Clinical Trial of Multiple Sclerosis

The primary objective of the trial is to determine whether short-term immunosuppression with mitoxantrone (Novantrone®) followed by chronic treatment with Glatiramer Acetate (Copaxone®) in comparison to treatment with Copaxone® for the same period of time without immunosuppression by mitoxantrone (Novantrone®) is well-tolerated and safe in patients with relapsing forms of MS as determined by clinical, laboratory and magnetic resonance imaging (MRI) parameters. The primary endpoints are tolerability and safety as measured by laboratory assessments and incidence of adverse experience. The secondary objective is to determine whether short-term immunosuppression with Novantrone® as an induction therapy accelerates the onset and enhances the efficacy of Copaxone® treatment in patients with relapsing forms of MS in 15 months of treatment based on MRI and clinical assessment.

The design of this trial is a multi-centered, randomized, two-arm, safety and tolerability study of open label induction of immunosuppression with 3 monthly treatments with Novantrone® followed by chronic treatment with Copaxone® versus chronic treatment with Copaxone® alone in patients with relapsing forms of MS. No blinding of induction is used. A blinded examiner determines the Expanded Disability Status Scale (EDSS) and Multiple Sclerosis Functional Composite (MSFC). One treatment arm (Group M-GA) receives a short (5 to 15 minutes) intravenous (IV) infusion of 12 mg/m$^2$ Novantrone® at Months 0, 1 and 2 and daily subcutaneous injections of 20 mg Copaxone® two weeks after the last scheduled infusion of Novantrone®. Treatment with Copaxone® continues for 12.5 months for a total treatment period of fifteen (15) months. The other treatment arm (Group GA) receives daily injections of 20 mg Copaxone® for a period of fifteen (15) months, but no Novantrone®. Fertile female patients also undergo a serum pregnancy test at screening and prior to each infusion.

Forty (40) patients are equally randomized into two groups: Twenty (20) patients in Group M-GA (Novantrone® followed by Copaxone®) and twenty (20) patients in Group GA (Copaxone® alone). Patients in Group M-GA who are unable to complete the induction phase are dropped and replaced. Those who are dropped from Group GA in the first three months are also replaced.

Participant inclusion criteria are as follows: 1) Male or female patients 18 to 55 years of age; 2) Patients having definite MS as determined by the McDonald criteria (Ann Neurol., July 2001) with relapsing disease course; 3) Patients having EDSS 0.0-6.5 (inclusive); 4) Patients having 1 or more T1 gadolinium-enhancing lesion(s) but not more than 15 gadolinium-enhancing lesions.

Participant exclusion criteria include the following: 1) Patients ever treated with GA or Mitoxantrone; 2) Patients treated with interferons or IV immunoglobulins (IVIg) in the previous 4 weeks prior to screening visits; 3) Patients treated with methotrexate, or azathioprine in the previous 6 months prior to screening visits; 4) Patients ever treated with cyclophosphamide, Total Lymphoid Irradiation (TLI), or cladribine for injection or anthracenediones or anthracyclines, or prior mediastinal radiotherapy; 5) Patients treated with IV or oral steroids within 30 days of baseline MRI; 6) Patients who are pregnant or lactating at the screening visit; 7) Patients having left ventricular ejection fraction (LVEF)<50%; 8) Patients using catheters or Foley catheters; 9) Patients having any other known significant systemic medical disease which may confound the evaluation of the study results such as amyotrophic lateral sclerosis (ALS), cervical spondylitic myelopathy, syphilis, arteritis, cerebellar syndrome (i.e., due to heredodegeneration), B12/folate deficiency, lyme disease, or human lymphotropic virus, type 1 (HTLV 1)-myelopathy; 10) Patients with immune deficiency or other medical condition that would preclude treatment with Mitoxantrone or GA; 11) Abnormal screening blood tests exceeding any of the following limits: Alanine transaminase (ALT)—twice the upper limit of normal (normal=4-36 U/L) (may be repeated once); Aspartate transaminase (AST)—twice the upper limit of normal (normal=0-35 U/L)(may be repeated once), Baseline neutrophil counts of <1500/mm$^3$, Total white blood cell count: <2300/mm$^3$, Platelet count: <80,000/mm$^3$, Creatinine: >1.5 mg/dl; Prothrombin time: >150% upper limit of normal (normal=11.0-12.5 secs.); 12) Patients having any medical or psychiatric conditions that would make the patient unsuitable for this research, as determined by the investigator.

Primary safety is measured by: 1) Monitoring of immunosuppression and drug toxicity: Complete blood count (CBC) with differential, Absolute lymphocyte count (ALC), Absolute neutrophil count (ANC), Platelet count (PLT), AST, ALT, Alkaline phosphatase, Total bilirubin, Blood urea nitrogen (BUN), Creatinine, Glucose, Electrolyte panel, Chest x-ray (CXR) and Urinalysis; 2) Monitoring of cardiac toxicity: electrocardiogram (EKG) (performed at screening) and Multiple Gated Acquisition (MUGA) for LVEF (performed at first pre-induction dose visit, month 2.5, and month 15).

The following secondary safety and efficacy parameters are measured by MRI (at screening and at months 6, 9, 12 and 15): 1) Number of Gadolinium-enhancing lesions; 2) Volume of Gadolinium-enhancing lesions; 3) Total T2-weighted lesion volume; 4) Total T1-weighted lesion volume; 5) Change in brain parenchymal volume as assessed by brain intracranial capacity ratio (BICCR); 6) Proportion of lesions that evolve into black holes >6 months after their appearance on MRI; 7) Atrophy (volume loss) associated with lesions >6 months after their appearance on MRI; 8) Total burden of disease using a semi-automated combined measures approach; 9) Change in mean MTR globally and for selected areas. Secondary clinical efficacy outcomes are measured by the following: 1) Relapse Rate (mean number of confirmed relapses in 15 months); 2) Proportion of relapse free patients; 3) Time to first relapse; 4) Change in MSFC performed at the first induction visit (baseline), following induction [month 3] and at each follow-up visit; 5) Change in EDSS: "area under the curve" (AUC) analysis and proportion with confirmed progression (1.0 change on EDSS in group with baseline EDSS <=5.0 or 0.5 change on EDSS in group with EDSS 5.5-6.5, lasting at least 3 months); 6) Changes in Performance Scales, Patient-Determined Disease Steps (PDDS), Quality of Life (SF-36®) and the Modified Fatigue Impact Scale (MFIS) (performed at first induction visit (baseline), following induction [month 3], months 6, 9, 12 and 15). A relapse is defined as the appearance or reappearance of one or more neurologic abnormalities persisting for at least 48 hours and occurring 30 days or more after the last confirmed relapse. A relapse is confirmed only when the patient's symptoms are accompanied by objective changes on the neurologic exam consistent with an increase of at least 0.5 step on the EDSS, two points on one of the seven functional systems or one point on two or more of the functional systems (FS). A change in bowel/bladder or cognitive function score is not solely responsible for the changes in either the EDSS or the FS scores. Events associated with fever are excluded.

Statistical power assessment for this study is based on the expected differences between the two study arms in the total number of enhancing lesions. The following underlying assumptions are used: 1) The efficacy end-point is the total number of enhancing lesions measured in months 12 and 15; 2) To maximize the effect size and to control variability, only active MRI patients with not more than 15 lesions at screening are eligible for the study; 3) The expected rate of enhancing lesions in an untreated active population is 3.68 lesions/scan; 4) The expected untreated individual patient's number of enhancing-lesions is derived from a Poisson distribution with a rate of $l_i$ (i=1, 2 . . . n) when this individual patient rate $l_i$ comes form a Gamma distribution with $2/q=Sl_i/n$ and $r=0.5$; 5) Two-sided alpha level of 5% is used to determine statistical significance; 6) The analysis model utilizes Quasi-Likelihood (over-dispersed) Poisson Regression (SAS® PROC GENMOD) with an "offset" based on the log of exposure; 7) Treatment effect of the group treated solely with Copaxone® is assumed to be 50%; 8) For a two-sided alpha level of 5% and a treatment effect of 85% in the induction group, a total of 20 patients per group yields a power of 75.2%; 9) For a two-sided alpha level of 5% and a treatment effect of 90% in the induction group, a total of 20 patients per group yields a power of 90.1%.

The statistical methodology for the safety and tolerability assessment, which is performed for the intent to treat (ITT) group, includes the following: 1) Adverse Events: The incidence and the frequency of adverse experiences is summarized and presented according to regulatory accepted dictionary. Data is tabulated by treatment group, gender, maximal severity, maximal outcome, maximal action taken and maximal relationship to the tested drug. Any serious adverse events and hospitalizations are listed and discussed individually; 2) Laboratory Tests: Frequency counts and data listings of laboratory tests outside the normal range are presented at each visit by treatment group. Descriptive statistics as well as changes from baseline are also presented by study group at each scheduled visit. Shift analysis from baseline to last observed value is also provided. Listings of measurements of potentially clinically significant laboratory test abnormalities is also presented by study group; 3) Cardiac Toxicity: Frequency counts and data listings of abnormalities as measured by EKG and MUGA for LVEF are presented by treatment group and visit; 4) Vital Signs: Frequency counts and data listings of potential clinically significant vital sign measurements are presented at each visit by treatment group. Descriptive statistics, as well as changes from baseline of vital signs, are also presented by study group at each scheduled visit; 5) Tolerability: Tolerability analysis is based on the percentage (%) of subjects who fail to complete the study, the percentage (%) of subjects who fail to complete the study because of Adverse Events, and the percentage (%) of subjects who fail to complete the study because of laboratory abnormalities. Time to withdrawal is presented by Kaplan-Meier curves. Statistical inference is performed using Cox's proportional hazards model to compare between the induction arm (Group M-GA) and the GA alone arm (Group GA).

The statistical methodology for the efficacy assessment is based on the number of enhancing lesions. The analysis model utilizes Quasi-Likelihood (over-dispersed) Poisson Regression (SAS® PROC GENMOD) with an "offset" based on the log of exposure. Screening count is used as a covariate. Treatment and center effect is included in the model. The center-by-treatment interaction term is tested using the −2 log likelihood ratio test. If the interaction term is not statistically significant (i.e. if p>0.05), it is excluded from the model. MRI statistical analysis is performed according to the following stages: Stage I: The total number of enhancing lesions counted in scans taken at months 12 and 15 is compared between groups; Stage II: The number of enhancing lesions detected in months 6 and 9 is compared between groups. Negative findings in stage I analysis do not necessarily imply that Mitoxantrone induction did not enhance the effect of GA. Type-I error adjustment for multiple comparisons is made according to Hochberg's step-up modification to Bonferroni's method.

The statistical methodology for the relapse rate is determined by analyzing the number of relapses over the 15 month period of treatment using Poisson regression as outlined above. Baseline EDSS score, prior 1-year number of relapses, age and gender are included in the model as covariates.

In comparison to the group receiving Copaxone® alone, the group receiving Novantrone® followed by Copaxone® exhibited comparable or greater performance on the primary and secondary safety measures. The administration of Novantrone® followed by Copaxone® results in comparable or greater results in the secondary efficacy outcome measures.

REFERENCES

U.S. Pat. No. 3,849,550, issued Nov. 19, 1974 (Teitelbaum, et al.).
U.S. Pat. No. 5,800,808, issued Sep. 1, 1998 (Konfino, et al.).
U.S. Pat. No. 5,858,964, issued Jan. 12, 1999 (Aharoni, et al.).
U.S. Pat. No. 5,981,589, issued Nov. 9, 1999 (Konfino, et al.).
U.S. Pat. No. 6,048,898, issued Apr. 11, 2000 (Konfino, et al.).
U.S. Pat. No. 6,054,430, issued Apr. 25, 2000 (Konfino, et al.).
U.S. Pat. No. 6,214,791, issued Apr. 10, 2001 (Arnon, et al.).
U.S. Pat. No. 6,342,476, issued Jan. 29, 2002 (Konfino, et al.).
U.S. Pat. No. 6,362,161, issued Mar. 26, 2002 (Konfino et al.).
Chabot and Yong, Interferon-β1b increases IL-10 in a model of T cell-microglia interaction: Relevance to MS, *Neurol.* 2000, 55: 1497-1505.

Chabot et al., Cytokine production in T lymphocyte-microglia interaction is attenuated by glatiramer acetate: A mechanism for therapeutic efficacy in multiple sclerosis, *Mult. Scler.*, in press.

Compston, Genetic susceptibility to multiple sclerosis, in *McAlpine's Mutiple Sclerosis*, Matthews, B. ed., London: Churchill Livingstone, 1991, 301-319.

Dal Canto, M. C., and H. L. Lipton. 1977. Multiple sclerosis. Animal model: Theiler's virus infection in mice. *Am. J. Path.* 88:497-500.

Filippi et al., Glatiramer acetate reduces the proportion of MS lesions evolving into black holes, *Neurol.*, 2001, 57:731-733.

Hafler and Weiner, M S: A CNS and systemic autoimmune disease, *Immunol. Today*, 1989, 10:104-107.

Johnson et al., Copolymer 1 reduces relapse rate and improves disability in relapsing-remitting multiple sclerosis: results of a phase III multicenter, double-blind placebo-controlled trial. The Copolymer 1 Multiple Sclerosis Study Group, *Neurol.*, 1995, 45:1268.

Lampert, Autoimmune and virus-induced demyelinating diseases. A review, *Am. J. Path.*, 1978, 91:176-208.

Martyn, The epidemiology of multiple sclerosis, in *McAlpine's Multiple Sclerosis*, Matthews, B., ed., London: Churchill Livingstone, 1991, 3-40.

McDonald et al., Recommended diagnostic criteria-for multiple sclerosis: guidelines from the International Panel on the diagnosis of multiple sclerosis. *Ann. Neurol.*, 2001, 50:121-127.

Multiple sclerosis: its diagnosis, symptoms, types and stages, 2003<http://www.albany.net/~tjc/multiple-sclerosis.html>.

Olsson, Immunology of multiple sclerosis, *Curr. Opin. Neurol. Neurosurg.*, 1992, 5:195-202.

Parkman, Graft-versus-host Disease, *Ann. Rev. Med.*, 1991, 42: 189-197.

Rodriguez, M. et al. 1987. Theiler's murine encephalomyelitis: a model of demyelination and persistence of virus. *Crit. Rev. Immunol.*, 7:325.

Teitelbaum et al., Suppression of Experimental Allergic Encephalomyelitis by a Synthetic Polypeptide, *Eur. J. Immunol.*, 1971, 1: 242-248.

Teitelbaum et al., Suppression of Experimental Allergic Encephalomyelitis with Basic Polymers, *Eur. J. Immunol.*, 1973, 3: 273-279.

"COPAXONE®" in *Physician's Desk Reference*, Medical Economics Co., Inc., Montvale, N.J., 2003, 3214-3218.

Guidance for Industry. In vivo drug metabolism/drug interaction studies—study design, data analysis, and recommendations for dosing and labeling, U.S. Dept. Health and Human Svcs., FDA, Ctr. for Drug Eval. and Res., Ctr. for Biologics Eval. and Res., Clin./Pharm., November 1999<http://www.fda.gov/cber/gdlns/metabol.pdf>.

"NOVATRONE®" in *Physician's Desk Reference*, Medical Economics Co., Inc., Montvale, N.J., 2003, 1747, 1749.

What is claimed is:

1. A method of treating a subject afflicted with a form of multiple sclerosis comprising administering to the subject 3 doses of 12 mg/m$^2$ mitoxantrone by intravenous infusion, at months 0, 1, and 2; followed 2 weeks later by daily subcutaneous injection of 20 mg glatiramer acetate, for at least 6 weeks.

2. The method of claim 1, wherein the form of multiple sclerosis is relapsing-remitting multiple sclerosis.

3. The method of claim 1, wherein the subject is a human being.

4. The method of claim 1, wherein the symptom is the frequency of relapses, the frequency of clinical exacerbation, or the accumulation of physical disability.

5. The method of claim 1 wherein the reduction of the accumulation of Gd-enhancing lesions in the subject is greater than the reduction of the accumulation of Gd-enhancing lesions in a subject treated with glatiramer acetate alone.

6. The method of claim 1 wherein the reduction in relapse rate in the subject is greater than the reduction in relapse rate in a subject treated with glatiramer acetate alone.

7. A package comprising
a first pharmaceutical composition comprising an amount of glatiramer acetate and a pharmaceutically acceptable carrier;
a second pharmaceutical composition comprising an amount of mitoxantrone and a pharmaceutically acceptable carrier; and
instructions for use of the first and second pharmaceutical compositions together to alleviate a symptom of a form of multiple sclerosis in a subject, comprising administering to the subject 3 doses of 12 mg/m$^2$ of mitoxantrone by intravenous infusion, at months 0, 1, and 2; followed 2 weeks later by daily subcutaneous injection of 20 mg glatiramer acetate, for at least 6 weeks.

* * * * *